(12) United States Patent
De Robillard (10) Patent No.: US 7,351,967 B2
(45) Date of Patent: Apr. 1, 2008

(54) SYSTEM AND METHOD FOR INSPECTING A SEMICONDUCTOR SAMPLE

(75) Inventor: Quentin De Robillard, Dresden (DE)

(73) Assignee: Advanced Micro Devices, Inc., Austin, TX (US)

( * ) Notice: Subject to any disclaimer, the term of this patent is extended or adjusted under 35 U.S.C. 154(b) by 141 days.

(21) Appl. No.: 11/386,623

(22) Filed: Mar. 22, 2006

(65) Prior Publication Data

US 2006/0219902 A1   Oct. 5, 2006

(30) Foreign Application Priority Data

Mar. 31, 2005   (DE) ............... 10 2005 014 794

(51) Int. Cl.
  *H01J 37/28* (2006.01)
(52) U.S. Cl. .................. 250/307; 250/310
(58) Field of Classification Search ............... 250/306, 250/307, 310, 311; 382/294, 295
  See application file for complete search history.

(56) References Cited

U.S. PATENT DOCUMENTS

| | | | | |
|---|---|---|---|---|
| 5,048,103 A * | 9/1991 | Leclerc et al. ............... | 382/294 |
| 5,077,473 A * | 12/1991 | Elings et al. ................ | 250/306 |
| 6,184,524 B1 * | 2/2001 | Brink et al. ................. | 250/305 |
| 6,448,555 B1 | 9/2002 | Hosokawa ................... | 250/310 |
| 6,774,362 B2 * | 8/2004 | Katagami et al. ........... | 250/307 |
| 6,888,139 B2 * | 5/2005 | Tsuneta et al. ............. | 250/311 |
| 7,127,126 B2 * | 10/2006 | Sakai et al. ................. | 382/294 |
| 7,197,168 B2 * | 3/2007 | Russo ........................ | 382/125 |
| 2002/0034338 A1 | 3/2002 | Askary ....................... | 382/295 |
| 2002/0199164 A1 | 12/2002 | Sengupta et al. ............. | 716/11 |
| 2003/0201393 A1 | 10/2003 | Tsuneta et al. ............. | 250/311 |
| 2005/0056784 A1 | 3/2005 | Subramaniam ............. | 250/311 |

* cited by examiner

*Primary Examiner*—John R. Lee
(74) *Attorney, Agent, or Firm*—Williams, Morgan & Amerson (57) ABSTRACT

The present invention relates to a system and method of inspecting a semiconductor sample. A plurality of scans of the semiconductor sample are recorded. Each of the scans comprises a spatially resolved measurement of a property of interest. At least one cross-correlation is calculated between at least two of the plurality of scans. For each of the plurality of scans, a respective shift value is calculated based on the at least one cross-correlation. The scans are superimposed with each other. In the superposition, each of the scans is shifted by the respective shift value. The shift values can be adapted to compensate a drift of the semiconductor sample which occurs while the scans are recorded. Hence, the present invention helps overcome problems caused by the drift.

24 Claims, 3 Drawing Sheets

SYSTEM AND METHOD FOR INSPECTING A SEMICONDUCTOR SAMPLE

BACKGROUND OF THE INVENTION

1. Field of the Invention

The present invention relates to the formation of integrated circuits, and, more particularly, to the inspection of semiconductor structures.

2. Description of the Related Art

Integrated circuits comprise a large number of individual circuit elements, such as transistors, capacitors and resistors, formed on a substrate. These elements are connected internally by means of electrically conductive lines to form complex circuits, such as memory devices, logic devices and microprocessors. The performance of integrated circuits can be improved by increasing the number of functional elements per circuit, in order to increase their functionality, and/or by increasing the speed of operation of the individual circuit elements. A reduction of feature sizes allows the formation of a greater number of circuit elements on the same area, hence allowing an extension of the functionality of the circuit, and also reduces signal propagation delays. The reduction of signal propagation times allows an increase of the speed of operation of the circuit elements. In modern integrated circuits, design rules of about 90 nm or less can be applied.

The formation of integrated circuits comprises a deposition of a large number of material layers on a semiconductor structure. The material layers are patterned by means of photolithography and etching in order to form the circuit elements and the components thereof.

Since characteristics of the material layers may strongly influence the performance of the integrated circuit, the formation of integrated circuits having small feature sizes requires a precise and reproducible deposition of material layers on a semiconductor substrate. Therefore, considerable effort is applied to the development of processes for the deposition of material layers. The development of such processes requires tools and methods for the characterization of the deposited material layers.

Frequently, electron microscopy is applied for this purpose. In addition to obtaining high resolution images of the semiconductor structure, electron microscopy may also be employed in determining a chemical composition of the semiconductor structure and material layers formed thereon. In the following, a method of inspecting a semiconductor structure according to the state of the art to determine the chemical composition of a material layer on the semiconductor structure will be described with reference to FIGS. 1a and 1b.

Figures 1A, 1B:
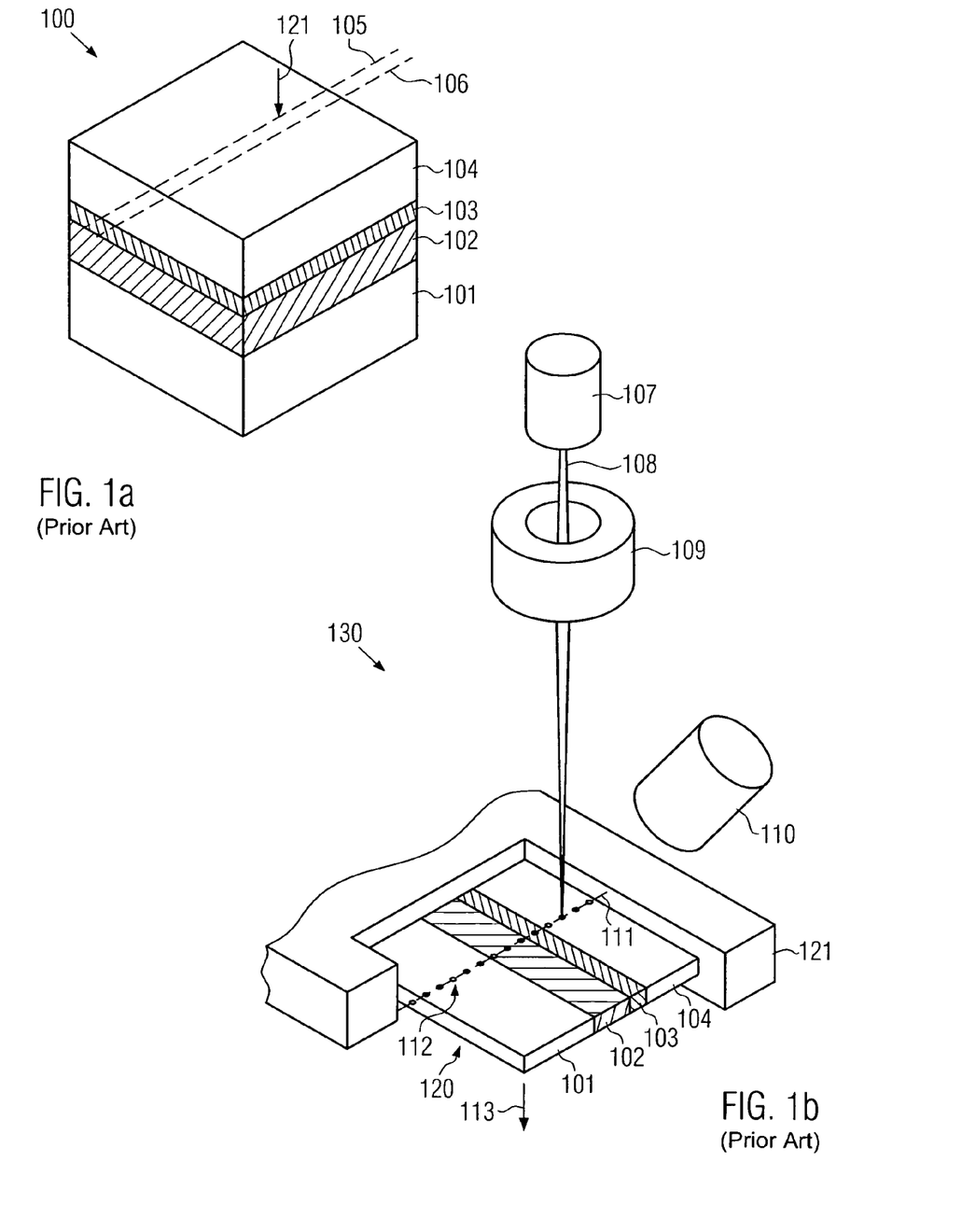
FIG. 1*a* shows a schematic perspective view of a section of a semiconductor structure comprising a plurality of material layers according to the state of the art.
FIG. 1*b* shows a schematic perspective view of an electron microscope adapted for an investigation of semiconductor structures according to the state of the art.

FIG. 1a shows a schematic perspective view of a section of a semiconductor structure 100. The semiconductor structure 100 comprises a substrate 101. On the substrate 101, a first material layer 102, a second material layer 103 and a third material layer 104 are formed. As persons skilled in the art know, the semiconductor structure 100 can be formed by performing a variety of known deposition methods, including chemical vapor deposition, plasma enhanced chemical vapor deposition and/or physical vapor deposition.

A semiconductor sample 120 (FIG. 1b) provided in the form of a cross-sectional specimen of the semiconductor structure 100 is prepared. To this end, the semiconductor structure 100 is cut along lines 105, 106 which can be substantially parallel to each other. A direction of the cuts indicated by an arrow 121 is substantially perpendicular to the surface of the substrate 101 and the material layers 102, 103, 104 formed thereon. Cutting the semiconductor structure 100 can be performed by means of mechanical milling techniques which are known to persons skilled in the art. After the cutting, a thickness of the semiconductor sample 120 may be reduced by means of advanced methods of ion beam milling and polishing techniques also known to persons skilled in the art.

FIG. 1b shows a schematic perspective view of an electron microscope 130. The electron microscope 130 comprises an electron source 107, an electron optic 109, a detector 110 and a sample holder 121. These components are provided inside a vacuum chamber (not shown). The semiconductor sample 120 is attached to the sample holder 121.

The electron optic 109 is configured to focus an electron beam 108 provided by the electron source 107 to the semiconductor sample 120. The detector 110 is configured to measure a property of interest, for example an energy loss of electrons of the electron beam 108 diffracted from the semiconductor sample 120 or a wavelength of X-rays produced by the semiconductor sample 120 in response to the irradiation with electrons. The measurement of the property of interest can be performed by means of methods known to persons skilled in the art.

The semiconductor sample 120 is scanned by the electron beam 108. To this end, the electron beam 108 and the semiconductor sample 120 are moved relative to each other. This can be done by mechanically moving the semiconductor sample 120 or by deflecting the electron beam 108. As persons skilled in the art know, the electron beam 108 can be deflected by applying an electric field or a magnetic field exerting a force to the electrons in the electron beam 108.

In the scanning process, the electron beam 108 can be directed to a plurality of points 112 arranged along a line 111 running across the semiconductor sample 111. The line 111 may run across portions of the substrate 101 and the material layers 102, 103, 104 exposed at a cut surface of the semiconductor sample 120. Whenever the electron beam 108 impinges on one of the plurality of points 112, the detector 110 is operated to measure the property of interest. For example, for each of the points 112, an X-ray spectrum or an electron energy loss spectrum can be recorded.

The property of interest may then be analyzed in order to derive characteristics of the semiconductor sample 120. In examples of methods of inspecting a semiconductor structure according to the state of the art, information concerning a chemical composition of the semiconductor sample 120 at each of the points 112 can be derived from recorded X-ray spectra and/or recorded electron energy loss spectra. Thus, a distribution of chemical elements along the line 111 can be obtained which may then be used, for example, to investigate a homogeneity of the material layers 102, 103, 104 and/or a sharpness of interfaces between the material layers 102, 103, 104.

In addition to the motion of the semiconductor sample 120 and the electron beam 108 relative to each other performed in the scanning of the semiconductor sample 120, an additional relative motion of the semiconductor sample 120 and the electron beam 108 which is denoted as "drift" may occur, as schematically indicated by arrow 113 in FIG. 1b. The drift can be caused by mechanical displacements in the electron microscope 130 which may be generated, for example, by thermal expansion of components thereof or by a relaxation of elastic stress in components of the electron microscope 130. Another source of the drift may be alterations of static electromagnetic fields in the electron microscope 130 or an environment thereof. Such electromagnetic fields may have an influence on trajectories of electrons in the electron beam 108.

The drift may interfere with the scanning of the semiconductor sample 120. Hence, erroneous results of the scanning process can be obtained. In particular, a drift of the semiconductor sample 120 in the direction of the scan may cause erroneous measurements of thicknesses of the material layers 102, 103, 104. Whereas a drift of the semiconductor sample in the direction of the scan can yield too large measured values of layer thicknesses, a drift of the semiconductor sample in a direction opposite to that of the scan may yield too small measured values of layer thicknesses. In order to avoid such errors, it has been proposed to correct the drift by a mechanical motion of the semiconductor sample 120. To this end, speed and direction of the drift can be determined and then the sample holder 121 may be moved in the opposite direction.

A problem of the above method of compensating for the drift is that the precision of mechanical drift correction is limited. Moreover, mechanical drift correction is typically performed stepwise after measuring the property of interest at a plurality of points, for example after measurement at about thirty points. Thereby, a drift occurring during the measurement at the plurality of points is not taken into account. Hence, only a partial correction of the drift is obtained. Hence, mechanical drift correction may be insufficient for precise measurements, in particular in case of a relatively large drift rate.

In view of the above problems, there is a need for a method of inspecting a semiconductor structure allowing a more precise correction of the drift.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

According to an illustrative embodiment of the present invention, a method of inspecting a semiconductor sample comprises recording a plurality of scans of the semiconductor sample. Each of the scans comprises a spatially resolved measurement of a property of interest. At least one cross-correlation between at least two of the plurality of scans is calculated. For each of the plurality of scans, a respective shift value is calculated based on the at least one cross-correlation. The scans are superimposed. In the superposition, each of the scans is shifted by the respective shift value.

According to another illustrative embodiment of the present invention, a method of inspecting a semiconductor sample comprises recording a plurality of scans of the semiconductor sample. The recording of each of the scans comprises scanning the semiconductor structure with an electron beam and measuring a response of the semiconductor structure to the electron beam. At least one cross-correlation between at least two of the plurality of scans is calculated. For each of the plurality of scans, a respective shift value is determined based on the at least one cross-correlation. The scans are added. In the addition, each of the scans is shifted by the respective shift value.

According to yet another illustrative embodiment of the present invention, a system for inspecting a semiconductor sample comprises an electron microscope adapted to record a plurality of scans of the semiconductor sample. Each of the scans comprises a spatially resolved measurement of a property of interest. An analyzer is adapted to calculate at least one cross-correlation between at least two of the plurality of scans and to determine a respective shift value for each of the plurality of scans based on the at least one cross-correlation. A superimposer is adapted to superimpose the scans. In the superposition, each of the scans is shifted by the respective shift value.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

The present invention is generally directed to methods and systems for inspecting a semiconductor structure wherein a drift is corrected by recording a plurality of scans of a semiconductor structure at a relatively short acquisition time per measurement point and then superimposing the scans. In the superposition, each of the scans is shifted by a shift value adapted to compensate for the drift.

The acquisition time can be adapted such that influences of the drift on the quality of the individual scans can substantially be neglected. Afterwards, the drift is determined from an investigation of the plurality of scans. To this end, at least one cross-correlation between at least two of the plurality of scans can be calculated and respective shift values adapted for a correction of the drift can be determined from the at least one cross-correlation. In the superposition, which may comprise an addition of the scans, each of the scans is shifted by the respective shift value. Thus, measurements of a property of interest obtained at substantially the same location of the semiconductor sample can be superimposed with each other.

Figure 2:
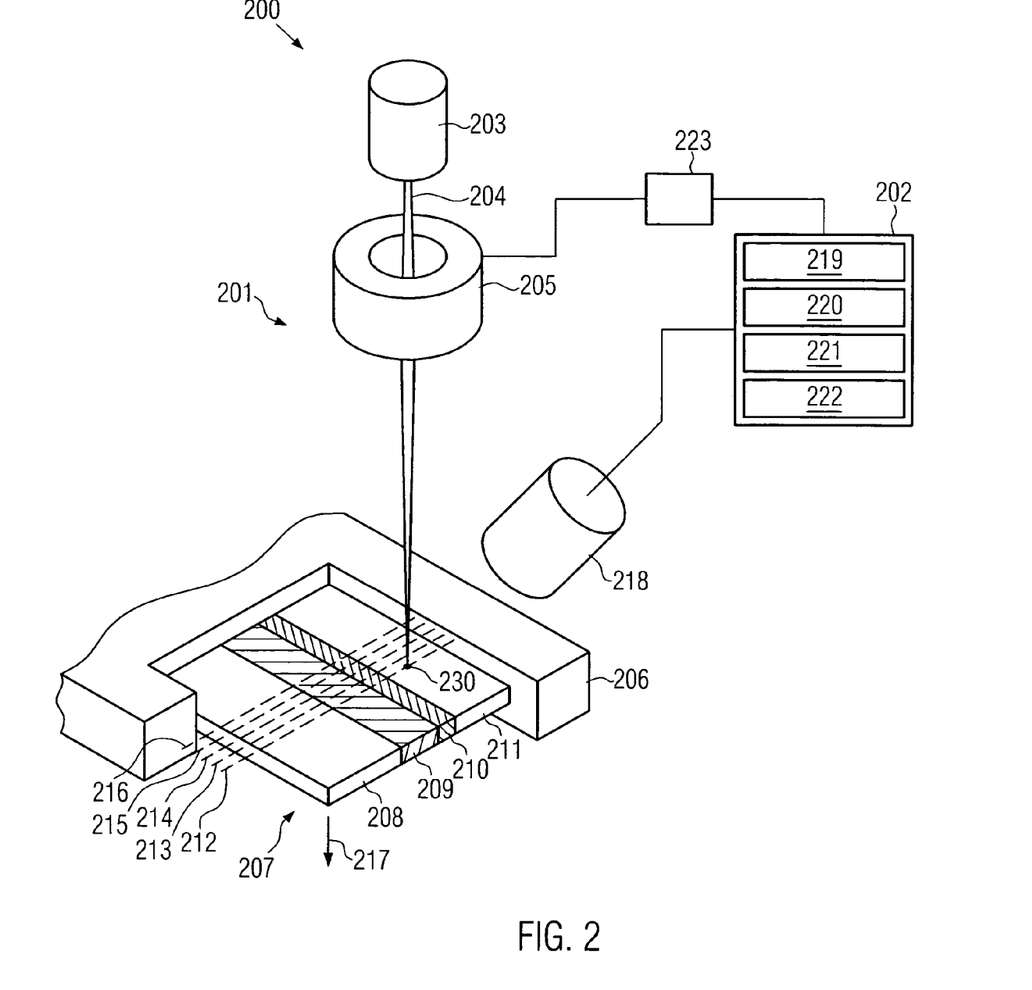
FIG. 2 shows a schematic perspective view of a system for inspecting a semiconductor sample according to an illustrative embodiment of the present invention.
Figure 3:
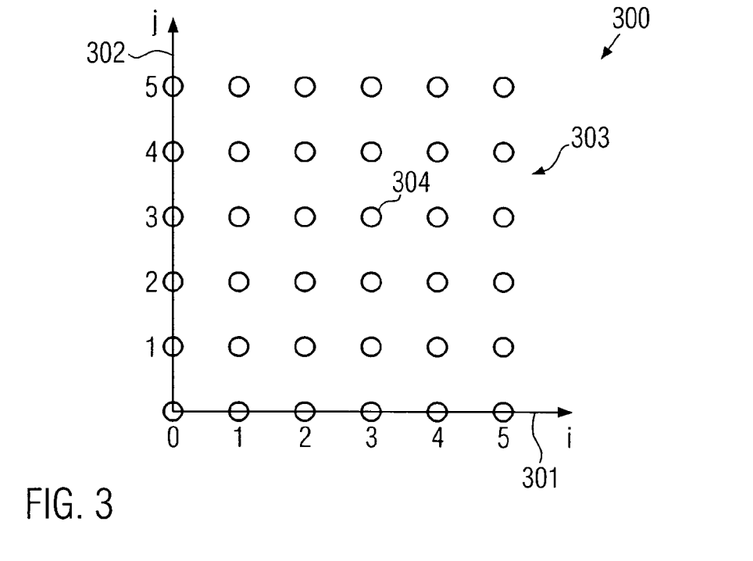
FIG. 3 shows a schematic diagram illustrating a raster of points of a two-dimensional scan of a semiconductor sample performed in a method according to an embodiment of the present invention.

Further embodiments of the present invention will now be described with reference to FIGS. 2–4. FIG. 2 shows a schematic perspective view of a system 200 for inspecting a semiconductor sample 207 according to the present invention.

The system 200 comprises an electron microscope 201. Similar to the electron microscope 130 described above with reference to FIG. 1b, the electron microscope 201 comprises an electron source 203. An electron optic 205 is adapted to focus an electron beam 204 emitted by the electron source 203 to the semiconductor sample 207. The semiconductor sample 207 may comprise a cross-sectional specimen of a semiconductor structure similar to the semiconductor structure 100 shown in FIG. 1a. More particularly, the semiconductor sample 207 may comprise portions of a substrate 208 on which a first material layer 209, a second material layer 210 and a third material layer 211 are formed. The semiconductor sample 207 can be provided in a sample holder 206 adapted to maintain the semiconductor sample 207 in a focus of the electron optic 205.

The electron microscope 201 further comprises a detector 218. In some embodiments of the present invention, the detector 218 can comprise an X-ray spectrometer of a type known to persons skilled in the art. The X-ray spectrometer can be adapted to measure a spectrum of X-rays emitted by the semiconductor sample 207 in response to an irradiation with the electrons in the electron beam 204. In other embodiments of the present invention, the detector 218 can comprise an energy-selective X-ray detector of a type known to persons skilled in the art and adapted to selectively measure an intensity of X-rays having a wavelength in a predefined wavelength range.

In further embodiments of the present invention, the detector 218 can comprise an energy-resolved electron detector of a type known to persons skilled in the art. The energy-resolved electron detector can be adapted to measure an energy distribution of electrons of the electron beam 204 diffracted from the semiconductor structure 207 and/or secondary electrons emitted by the semiconductor structure 207 in response to the irradiation with the electrons of the electron beam 204. In other embodiments of the present invention, the energy-resolved electron detector can be configured to selectively measure an intensity of electrons having an energy in a predefined energy range.

The detector 218 and the electron source 203 need not be arranged on the same side of the semiconductor sample 207 as shown in FIG. 2. In other embodiments of the present invention, the detector 218 can be arranged on a side of the semiconductor sample 207 opposite to the electron source 203 and the electron optics 205.

In addition to the electron microscope 201, the system 200 for inspecting a semiconductor sample can comprise an analyzer 202 and a control unit 223. The analyzer 202 can comprise a correlation calculator 219, a shift value calculator 220, a shifter 221 and a super-imposer 222. The control unit 223 can be adapted to control the analyzer 202 and the electron microscope 201. In some embodiments of the present invention, the analyzer 202 and the control unit 223 can be provided in the form of a digital computer known to persons skilled in the art.

In the following, a method of inspecting a semiconductor sample according to the present invention, which, in some embodiments, can be performed by means of the system 200, will be described. The method comprises providing the semiconductor sample 207 and inserting the semiconductor sample 207 into the sample holder 206.

In some embodiments of the present invention, the semiconductor sample 207 comprises a cross-sectional specimen of a semiconductor structure similar to the semiconductor structure 100 shown in FIG. 1a. The semiconductor sample 207 can be provided by cutting the semiconductor structure along parallel lines similar to the lines 105, 106 shown in FIG. 1a, for example by means of mechanical milling known to persons skilled in the art. A direction of the cuts can be substantially perpendicular to a material layer provided in the semiconductor structure. After the cutting, a thickness of the semiconductor sample 207 may be reduced, for example by means of advanced ion beam milling and polishing methods. Typically, the semiconductor sample may have a thickness in a range from about 30-120 nm.

Thereafter, the electron source 203 is operated to provide the electron beam 204. The electron beam 204 is focused to a point 230 on the surface of the semiconductor sample 207. The electrons of the electron beam 204 impinge on a portion of the semiconductor sample 207 in the vicinity of the point 230 and interact with the semiconductor sample 207.

Due to the interaction between the electrons and the semiconductor sample 207, a fraction of the electrons may be scattered. Additionally, energy may be transferred from the electrons in the electron beam 204 to electrons in the semiconductor sample 207. Thus, electrons may be removed from bound states in the semiconductor sample 207 and may leave the semiconductor sample 207. The bound states may then be reoccupied by other electrons. Energy released in the reoccupation of the bound states may be emitted in the form of X-rays. Since the electron beam 204 is focused to the point 230, interactions between the electrons of the electron beams 204 and the semiconductor sample 207 occur substantially only at the point 230.

The energy distribution of scattered and secondary electrons as well as the spectrum of the X-rays can reveal information regarding a property of interest. The energy distribution of the scattered and secondary electrons can comprise peaks at particular electron energies. A height of such peaks can be representative of a concentration of a particular chemical element and/or the occurrence of a particular kind of chemical bond at the point 230. Similarly, the X-ray spectrum can comprise peaks at particular wavelengths which are characteristic for the presence of particular chemical elements in the semiconductor sample 207.

The property of interest can be determined from investigations of the scattered and secondary electrons and/or from the X-rays generated in the semiconductor structure 207. In some embodiments of the present invention, the property of interest can comprise a number of electrons received from the point 230 and having an energy in a predefined range. In embodiments wherein the detector 218 is adapted to measure an energy distribution of scattered and/or secondary electrons, the number of electrons having an energy in the predefined range can be determined by integrating the measured energy distribution over the predefined energy range. In other embodiments wherein the detector 218 is adapted to selectively measure an intensity of electrons having an energy in the predefined range, such an integration can be omitted.

In further embodiments of the present invention, the property of interest can comprise a number of X-ray photons received from the point 230 and having a wavelength in a particular range. In embodiments wherein the detector 218 comprises an X-ray spectrometer, the property of interest can be determined by integrating a measured X-ray spectrum in the wavelength range of interest. In other embodiments wherein the detector 218 comprises an energy-selective X-ray detector adapted to selectively measure an intensity of X-rays having a wavelength in the predefined wavelength range, such an integration may be omitted.

In one specific embodiment of the present invention, the property of interest can comprise an amount of diffracted electrons having an energy in a range from about 1.5-300 keV less than the energy of the electrons in the electron beam 204. The electrons in the electron beam 204 may have an energy of about 120 keV, of about 200 keV or about 300 keV. In another embodiment, the property of interest can comprise an intensity of X-rays having an energy of about 300 keV or less. Examples of energy ranges of electrons and wavelength ranges of X-rays representative for a concentration of particular chemical elements and/or an occurrence of particular kinds of chemical bonds are known to persons skilled in the art.

The semiconductor sample 207 is scanned with the electron beam 204. The scanning of the semiconductor sample 207 can be controlled by the control unit 223. In the scanning process, the point 230 where the electron beam 204 impinges on the semiconductor sample 207 is moved across the semiconductor sample 207. To this end, the electron beam 204 and the semiconductor sample 207 can be moved relative to each other. In some embodiments of the present invention, the relative motion of the electron beam 204 and the semiconductor sample 207 is effected by deflecting the electron beam 204 by means of an electric or magnetic field, which may, in some embodiments, be generated by the electron optic 205. In other embodiments, the relative motion of the electron beam 204 and the semiconductor sample 207 can be effected by mechanically shifting the semiconductor sample. As persons skilled in the art know, a mechanical motion of the semiconductor sample 207 can be effected by applying an electric voltage to piezoelectric crystals (not shown) provided in the sample holder 206, wherein the semiconductor sample 207 is connected to the piezoelectric crystals.

In some embodiments of the present invention, a one-dimensional scan of the semiconductor sample 207 is performed. In such embodiments, the point 230 is moved along a line 212 which may be substantially perpendicular to one or more material layers 209, 210, 211 formed in the semiconductor sample 207. During the scanning process, the property of interest can be measured at a plurality of points arranged along the line 212. Thus, a spatially resolved measurement of the property of interest comprising one-dimensional data is obtained. A resolution of the spatially resolved measurement is determined by a distance between the points.

In other embodiments, a two-dimensional scan can be performed. FIG. 3 shows a schematic diagram illustrating a raster 303 of points. A first coordinate axis 301 and a second coordinate axis 302 represent positions on the surface of the semiconductor sample 207. A first index "i" enumerates columns of the points 303 arranged along the first coordinate axis 301. A second index "j" enumerates lines of the points 303 arranged along the second coordinate axis 302. Each of the points 303 can be characterized by a pair of values of the indices i, j. For example, a point 304 is characterized by indices i=j=3.

As the scan is performed, the point 230 where the electron beam 204 impinges on the semiconductor sample 207 is sequentially moved to the points of the raster 303. In some embodiments of the present invention, the points of the raster 303 can be sampled linewise. To this end, the point 230 is first sequentially moved to the line of points of the raster 303 having index j=0. Then, the point 230 is sequentially directed to lines of points having an increasing index j.

At each of the points of the scan, the property of interest can be measured. Thus, a spatially resolved measurement of the property of interest comprising two-dimensional data can be obtained.

In one specific embodiment wherein the property of interest comprises an amount of electrons in a particular energy range, the scanning process can have a duration of about 200 seconds or less, of about 100 seconds or less or of about 50 seconds or less. In another embodiment wherein the property of interest comprises an intensity of X-rays having a wavelength in a particular wavelength range, the scanning process may have a duration of about 200 minutes or less, of about 100 minutes or less or of about 50 minutes or less.

Similar to the method of inspecting a semiconductor structure according to the state of the art described above with reference to FIGS. 1a and 1b, in the method of inspecting a semiconductor sample according to the present invention, a drift may occur, as schematically indicated in FIG. 2 by arrow 217. In some embodiments of the present invention, a speed of the scanning process can be adapted such that a relative shift of the electron beam 204 and the semiconductor sample 207 caused by the drift can substantially be neglected compared to the resolution of the spatially resolved measurement at typical drift rates.

A plurality of scans of the semiconductor sample 207 similar to the scanning process described above is performed. In each of the scans, a spatially resolved measurement of the property of interest is obtained. Due to the drift, the individual scans are shifted relative to each other.

In case of a one-dimensional scan wherein the property of interest is measured at a plurality of points arranged along a line, the drift may have a component transverse to the line. Hence, in case a first of the plurality of scans is performed along the line 212, other scans of the plurality of scans are performed along lines 213, 214, 215, 216 being substantially parallel to the line 212. Additionally, the drift may have a component parallel to the direction of the scans.

If the scans are performed in a direction substantially perpendicular to at least one of the material layers 209, 210, 211 of the semiconductor structure 207, due to a different composition of the material layers 209, 210, 211, the property of interest may exhibit relatively large fluctuations in the direction of the scans. In the direction transverse to the scans, however, the fluctuations of the property of interest can be considerably lower. Hence, the transverse component of the drift may have a relatively small influence on the property of interest measured in the individual scans.

Figure 4:
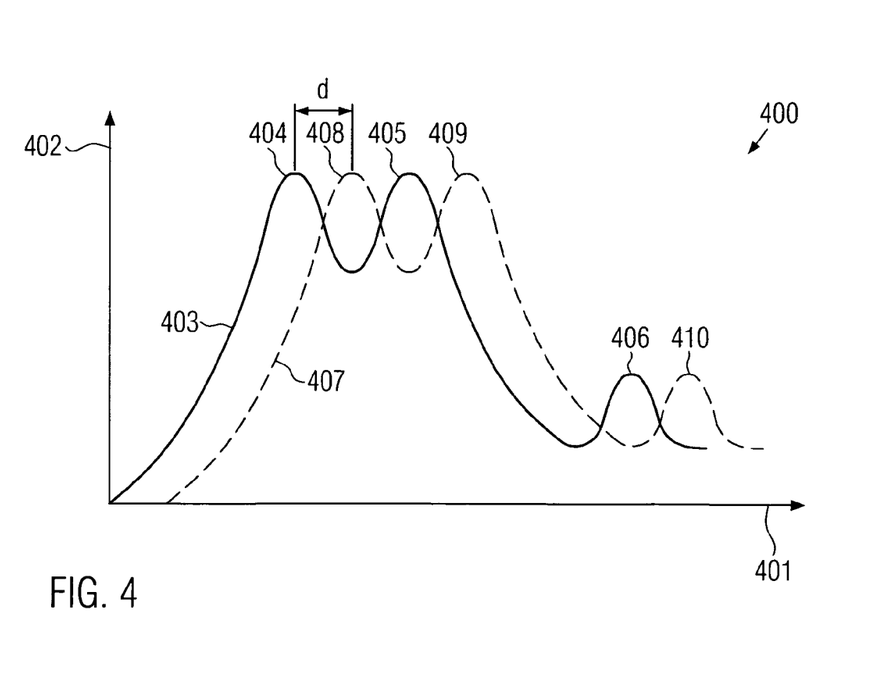
FIG. 4 shows a schematic diagram illustrating scans of a semiconductor sample performed in a method according to an embodiment of the present invention.

FIG. 4 shows a schematic diagram 400 illustrating one-dimensional scans of a semiconductor sample obtained in the presence of a drift. The diagram comprises a first coordinate axis 401 and a second coordinate axis 402. The first coordinate axis 401 represents a distance from a first point of each of the scans at which the spatially resolved measurement is started. The second coordinate axis 402 represents values of the property of interest measured in each of the scans.

A first curve 403 exemplifies values of the property of interest measured in a first scan. The first measurement curve 403 may comprise a plurality of peaks 404, 405, 406 representing locations on the semiconductor sample 207 at which the property of interest assumes relatively large values. A second curve 407 exemplifies values of the property of interest measured in a second scan. Similar to the first curve 403, the second curve 407 comprises peaks 408, 409, 410. Due to the component of the drift in the direction of the first scan and the second scan, the peaks 408, 409, 410 are shifted relative to the peaks 404, 405, 406 by a distance "d."

Similarly, in embodiments of the present invention wherein a plurality of two-dimensional scans of the semiconductor sample 207 are performed, characteristic features of the property of interest on the surface of the semiconductor sample 207 are shifted relative to each other in the individual scans. The shift of the characteristic features may have both a component in the direction of the first coordinate axis 301 and a component in the direction of the second coordinate axis 302 (FIG. 3).

At least one cross-correlation between at least two of the plurality of scans is calculated. This can be done by means of the correlation calculator 219 of the analyzer 202.

In embodiments of the present invention wherein the scans comprise one-dimensional data, in each of the scans, the property of interest is measured at a plurality of points arranged along a line. In the following, let $f_i$ denote the value of the property of interest measured at an i-th one of the plurality of points of the first scan, whereas $g_j$ denotes the value of the property of interest measured at a j-th one of the plurality of points of the second scan. The indices i, j enumerate the points of the respective scans. i=0 denotes a first point of the first scan and i=n−1 denotes a last point of the first scan, wherein n is the number of points of each of the scans. Similarly, j=0 denotes a first point of the second scan and j=n−1 denotes a last point of the second scan. For values of the indexes i, j less than zero or greater than n−1, one may set $f_i$ and $g_j$ to zero.

The cross-correlation between the first scan and a second scan may then be calculated as:

$$c_j = \sum_{k=0}^{n-1} f_k g_{j+k} \quad (1)$$

wherein the index j can assume both positive and negative values. The cross-correlation corresponds to a sum of products of the values of the property of interest measured in the first and the second scan, wherein the second scan is shifted by a distance determined by the index j. Positive values of the index j correspond to a shift of the second scan into the direction from the first point of the second scan towards the last point of the second scan, whereas negative values of the index j correspond to a shift of the second scan into the opposite direction. j=0 corresponds to no shift of the first scan at all.

In other embodiments of the present invention wherein the scans comprise two-dimensional data, the cross-correlation between a first of the plurality of scans and a second of the plurality of scans can be calculated as:

$$c_{i,j} = \sum_{k=0}^{n-1} \sum_{l=0}^{n-1} f_{k,l} g_{k+i,l+j} \quad (2)$$

wherein $f_{k,l}$ denotes a value of the property of interest measured in the first scan at a point of the raster having a first index k and a second index l, and $g_{k+i, l+j}$ denotes a value of the property of interest measured in the second scan at a point of the raster having a first index k+i and a second index l+j. For values of k+i and l+j less than zero or greater than n−1, $g_{k+i, l+j}$ may be set to zero. The pair of indices (i, j) denote a shift of the second scan relative to the first scan.

As persons skilled in the art know, the cross-correlation can be calculated efficiently by means of a fast Fourier transform. Alternatively, the cross-correlation may be calculated directly by performing the summation according to Equation (1) or Equation (2), respectively.

The cross-correlation between the first scan and the second scan assumes large values if the second scan is shifted such that large values of the property of interest measured in the first scan coincide with large values of the property of interest measured in the second scan. For example, in case the values of the property of interest measured in a one-dimensional scan are given by the curves 403, 407, the cross-correlation assumes a maximum for a value of the index j corresponding to a shift of the first scan by the distance d into a direction opposite to that of the first coordinate axis 401 such that the peaks 404, 408, the peaks 409, 405 as well as the peaks 406, 410 coincide. Similarly, the cross-correlation between two two-dimensional scans assumes large values if the second scan is shifted by such distances in the direction of the first coordinate axis 301 and the direction of the second coordinate axis 302, respectively, that characteristic features of the property of interest in the first scan and the second scan coincide.

A respective shift value is calculated for each of the plurality of scans based on the at least one cross-correlation. In embodiments of the present invention wherein one-dimensional scans are performed, cross-correlations between a first one of the plurality of scans and each of the other of the plurality of scans can be calculated. Subsequently, for each of the cross-correlations, a value of the index j which maximizes the respective cross-correlation is calculated by means of numerical methods known to persons skilled in the art. The first scan then obtains a shift value of zero. Each of the other scans obtains a shift value $j_k$ corresponding to the value of the index j which maximizes the correlation between the first scan and the other scan.

In other embodiments wherein one-dimensional scans are performed, a cross-correlation between the first of the plurality of scans and the last of the plurality of scans is calculated. Then, a value $j_{max}$ of the index j which maximizes the cross-correlation is determined by means of numerical methods known to persons skilled in the art. Subsequently, the first scan obtains a shift value of zero and the last scan obtains a shift value of $j_{max}$. In order to determine shift values for the other scans, an interpolation between the shift value zero and the shift value $j_{max}$ can be performed. The interpolation can be a linear interpolation wherein the shift value for a k-th one of the scans can be determined in accordance with:

$$j_k = \text{round}\left(\frac{j_{\max}(k-1)}{N-1}\right) \quad (3)$$

wherein N is the number of scans performed and round(x) denotes a rounded value of a number x.

A linear interpolation between the shift values for the first scan and the last scan is particularly advantageous if the drift is substantially a linear motion at constant speed of the semiconductor sample 207 and the electron beam 204 relative to each other. In this case, the shift between the first scan and another scan caused by the drift increases linearly with the time between the recording of the first scan and the other scan. The value $j_{max}$ of the index j is representative for the drift speed: the greater the drift speed, the greater is $j_{max}$.

In embodiments of the present invention wherein two-dimensional scans are performed, a respective shift value comprising a pair of indices $(i_k, j_k)$ can be determined by calculating cross-correlations between a first of the plurality of scans and each of the other of the plurality of scans. The first scan obtains the shift value (0, 0). Each of the other scans obtains a shift value corresponding to the pair $(i_k, j_k)$ of indices which maximizes the cross-correlation between the respective scan and the first scan.

In other embodiments wherein two-dimensional scans are performed, the cross-correlation between the first of the plurality of scans and the last of the plurality of scans can be calculated. Then, a pair $(i_{max}, j_{max})$ of indices which maximizes the cross-correlation is determined, which can be done by means of numerical methods known to persons skilled in the art. The first scan obtains the shift value (0, 0) and the last scan obtains the shift value $(i_{max}, j_{max})$. Shift values $(i_k, j_k)$ for the other scans can be determined by means of an interpolation according to the following mathematical expressions, wherein N denotes the number of scans performed and the index k enumerates the individual scans.

$$i_k = \text{round}\left(\frac{i_{\max}(k-1)}{N-1}\right) \quad (4)$$

$$j_k = \text{round}\left(\frac{j_{\max}(k-1)}{N-1}\right) \quad (5)$$

The scans are superimposed. In the superposition, each of the scans is shifted by the respective shift value $j_k$. The superposition and the shifting of the scans can be performed by means of the superimposer 222 and the shifter 221 of the analyzer 202, respectively.

In embodiments of the present invention wherein one-dimensional scans are performed, the shifting of a scan can be performed by replacing the value $f_i$ of the property of interest measured at the i-th point of the scan with the value $f_{i+j_k}$ of the property of interest measured at the $(i+j_k)$-th point of the scan. The replacement is performed for each point of the scan. For values of $i+j_k$ less than zero or greater than n−1, the value $f_i$ can be replaced with the value zero.

In embodiments wherein two-dimensional scans are performed, the shifting of a scan can be performed by replacing the value $f_{i,k}$ of the property of interest measured at a point of the scan characterized by a pair of indices (i, j) with the value $f_{i+i_k,\ j+j_k}$ of the property of interest measured at the point of the scan characterized by index pair $(i+i_k, j+j_k)$. The replacement is performed for each point of the scan. For values of $i+i_k$ or $j+j_k$ less than zero or greater than n−1, the value $f_{i,j}$ can be replaced with the value zero.

The superposition of the scans can comprise an addition of measured values of the property of interest contained in the shifted scans. In other embodiments of the present invention, the superposition of the scans can comprise a calculation of an average of measured values of the property of interest contained in the individual scans. The superposition of the scans may reduce noise effects which may be caused by the relatively short acquisition time of the individual scans. Due to the shifting of each of the scans by the respective shift value, the shift of semiconductor sample 207 relative to the electron beam 204 caused by the drift can substantially be compensated without there being a requirement to perform a drift correction while the semiconductor sample 207 is scanned.

A method of inspecting a semiconductor sample according to the present invention may further comprise a determination of at least one component of the drift speed of the semiconductor sample 207.

In embodiments of the present invention wherein the scans comprise one-dimensional data, a component of the drift speed may be determined from a value $j_{max}$ of the index j which maximizes the cross-correlation $c_j$ between a first scan and a second scan defined in equation (1) in accordance with the following equation:

$$v = \frac{j_{\max}s}{t} \quad (6)$$

wherein s denotes a spacing between the individual points of the scans and t is a time elapsed between the first scan and the second scan.

In embodiments of the present invention wherein the scans comprise two-dimensional data, a first component $v_1$ of the drift in the direction of the first coordinate axis 301 and a second component $v_2$ of the drift in the direction of the second coordinate axis 302 can be determined from values $i_{max}, j_{max}$ of the indices i, j which maximize the cross-correlation $c_{i,j}$ between the first scan and the second scan defined in equation (2).

$$v_1 = \frac{i_{\max}s}{t} \quad (7)$$

$$v_2 = \frac{j_{max}s}{t} \quad (8)$$

wherein s denotes a spacing between the points of the scans and t is a time elapsed between the first scan and the second scan The drift speed may be used to correct distances measured from the scans. The correction of the measured distances may comprise a rescaling of the measured distances by a factor which is based on the determined drift speed.

In embodiments wherein the scans comprise one-dimensional data, a corrected distance $d_{corr}$ which may, for example, comprise a thickness of one of the material layers 209, 210, 211, can be calculated from a measured distance $d_{measured}$ in accordance with the following equation:

$$d_{corr} = d_{measured}\left(1 - \frac{\tau v}{s}\right) \quad (9)$$

Here, $\tau$ denotes the time interval between subsequent measurements of the property of interest in the scan.

In embodiments of the present invention wherein two-dimensional scans are performed and the points of the raster 303 are sampled linewise, as described above with reference to FIG. 3, distances measured from the scans in the direction of the first coordinate axis 301 may be rescaled in accordance with equation (9), wherein the first component $v_1$ of the drift speed is inserted as value v of the drift speed. Distances measured from the scans in the direction of the second coordinate axis 302 may be rescaled in accordance with the following equation:

$$d_{corr} = d_{measured}\left(1 - \frac{n\tau v_2}{s}\right) \quad (10)$$

wherein n denotes the number of points per line.

In other embodiments of the present invention, the individual scans are subjected to a transformation adapted to invert distortions of the scans caused by the drift. In embodiments of the present invention wherein the scans comprise one-dimensional data, the transformation can comprise a rescaling of the scans by a factor $(1-\tau v/s)$. If the drift is in the direction of the scan, the rescaling comprises a contraction of the scan. Conversely, a drift in the opposite direction may be taken into account by a dilation of the scans.

In embodiments wherein the scans comprise two-dimensional data, the scans may be subjected to an affine transformation comprising a rescaling of the lines by a factor $(1-\tau v_1/s)$ and a rescaling of the columns by a factor $(1-n\tau v_2/s)$.

In further embodiments of the present invention, the superimposed scans may be subjected to a transformation adapted to correct the drift after the superposition of the scans.

The present invention is not restricted to embodiments wherein no mechanical drift correction is performed. In other embodiments of the present invention, a mechanical drift correction may be performed while the plurality of scans are recorded. Advantageously, this allows longer acquisition times for the individual scans, which may help reduce inaccuracies of the shift values caused by noise of the individual scans.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of inspecting a semiconductor sample, comprising:
    recording a plurality of scans of said semiconductor sample, each of said scans comprising a spatially resolved measurement of a property of interest;
    calculating at least one cross-correlation between at least two of said plurality of scans;
    determining a respective shift value for each of said plurality of scans based on said at least one cross-correlation; and
    combining said scans, each of said scans being shifted by said respective shift value in said combination.

2. The method of claim 1, wherein said recording of said scans comprises directing an electron beam to said semiconductor sample.

3. The method of claim 2, wherein said recording of said scans comprises moving said electron beam and said semiconductor sample relative to each other.

4. The method of claim 1, wherein said measurement of said property of interest comprises determining at least one of an electron energy loss spectrum and an X-ray spectrum.

5. The method of claim 1, further comprising providing said semiconductor sample, said provision of said semiconductor sample comprising preparing a cross-sectional specimen of a semiconductor structure.

6. The method of claim 5, wherein said preparation of said cross-sectional specimen comprises cutting said semiconductor structure substantially perpendicularly to a material layer provided in said semiconductor structure.

7. The method of claim 1, further comprising calculating cross-correlations between one of said plurality of scans and each of the other ones of said plurality of scans.

8. The method of claim 1, wherein said determination of said respective shift value comprises determining a maximum of said at least one cross-correlation.

9. The method of claim 1, wherein said determination of said respective shift value comprises determining a quantity representative of a drift speed of said semiconductor sample.

10. The method of claim 1, wherein combination of said scans comprises at least one of an addition, a calculation of an average, and a calculation of a median of measured values of said property of interest.

11. A method of inspecting a semiconductor sample, comprising:
    recording a plurality of scans of said semiconductor sample, said recording of each of said scans comprising scanning said semiconductor structure with an electron beam and measuring a response of said semiconductor structure to said electron beam;
    calculating at least one cross-correlation between at least two of said plurality of scans;

determining a respective shift value for each of said plurality of scans based on said at least one cross-correlation; and adding said scans, each of said scans being shifted by said respective shift value in said addition.

12. The method of claim 11, wherein said response of said semiconductor structure comprises at least one of an electron energy loss spectrum and an X-ray spectrum.

13. The method of claim 11, further comprising providing said semiconductor sample, said provision of said semiconductor sample comprising preparing a cross-sectional specimen of a semiconductor structure.

14. The method of claim 13, wherein said preparation of said cross-sectional specimen comprises cutting said semiconductor structure substantially perpendicularly to a thickness direction of a material layer provided in said semiconductor structure.

15. The method of claim 11, further comprising calculating cross-correlations between one of said plurality of scans and each of the other ones of said plurality of scans.

16. The method of claim 11, wherein said determination of said respective shift value comprises determining a maximum of said at least one cross-correlation.

17. The method of claim 11, wherein said determination of said respective shift value comprises determining a quantity representative of a drift speed of said semiconductor sample.

18. A system for inspecting a semiconductor sample, comprising:

an electron microscope adapted to record a plurality of scans of said semiconductor sample, each of said scans comprising a spatially resolved measurement of a property of interest;

an analyzer adapted to calculate at least one cross-correlation between at least two of said plurality of scans and to determine a respective shift value for each of said plurality of scans based on said at least one cross-correlation; and an superimposer adapted to combine said scans, each of said scans being shifted by said respective shift value in combination.

19. The system of claim 18, wherein said electron microscope comprises at least one of an energy-resolved electron detector and an X-ray spectrometer.

20. The system of claim 18, wherein said analyzer is adapted to calculate cross-correlations between one of said plurality of scans and each of the other ones of said plurality of scans.

21. The method of claim 1, comprising performing a transposition on said combination of scans after the combination of the scans.

22. The method of claim 21, wherein performing the transposition on said combination of scans after the combination of the scans comprises performing the transposition based on at least one drift speed associated with the scans.

23. The method of claim 1, wherein combining said scans comprises combining values of the measurements of the property of interest associated with each scan.

24. The method of claim 23, wherein combining said scans comprises combining values of the measurements of the property of interest associated with each scan obtained at substantially the same location of the semiconductor sample.

* * * * *